United States Patent [19]
Saito et al.

[11] Patent Number: 5,054,491
[45] Date of Patent: Oct. 8, 1991

[54] ULTRASONIC ENDOSCOPE APPARATUS

[75] Inventors: Yoshitake Saito, Kunitachi; Kenji Hirooka, Hachioji, both of Japan

[73] Assignee: Olympus Optical Co., Ltd., Tokyo, Japan

[21] Appl. No.: 417,485

[22] Filed: Oct. 5, 1989

[30] Foreign Application Priority Data

Oct. 17, 1988 [JP] Japan ............................ 63-259495
Jun. 28, 1989 [JP] Japan ............................ 1-163722

[51] Int. Cl.⁵ .............................................. A61B 8/12
[52] U.S. Cl. .................................... 128/662.06; 128/4
[58] Field of Search .................. 128/4, 661.07–661.10, 128/662.06

[56] References Cited

U.S. PATENT DOCUMENTS

| | | | |
|---|---|---|---|
| 4,062,237 | 12/1977 | Fox ............................ | 128/662.04 X |
| 4,605,009 | 8/1986 | Pourcelot et al. ............. | 128/662.06 |
| 4,819,650 | 4/1989 | Goldstein .................... | 128/662.06 X |
| 4,869,256 | 9/1989 | Kanno et al. ................ | 128/662.06 X |

FOREIGN PATENT DOCUMENTS

| | | |
|---|---|---|
| 0046987 | 3/1982 | European Pat. Off. . |
| 0051167 | 5/1982 | European Pat. Off. . |
| 0139574 | 5/1985 | European Pat. Off. . |
| 3336803 | 10/1983 | Fed. Rep. of Germany . |
| 3435563 | 5/1985 | Fed. Rep. of Germany . |
| 3639981 | 5/1988 | Fed. Rep. of Germany . |

Primary Examiner—Francis Jaworski
Attorney, Agent, or Firm—Stevens, Davis, Miller & Mosher

[57] ABSTRACT

In an ultrasonic endscope apparatus for observing an optical image of a cavity of a body under inspection by forming the optical image with the aid of an objective lens arranged in a distal end of an insertion section of an endoscope and by transmitting the optical image by means of an image guide and for observing an ultrasonic sectional image by arranging an ultrasonic vibrating element in the distal end of the insertion section, a distance between the objective lens and the cavity is measured by detecting a first echo reflected by the cavity, image data representing a locus of a section line of the ultrasonic sectional image is derived in accordance with the measured distance, the image of the section line is displayed on a display device, and the displayed image of the section line is monitored in the superimposed manner with the optical image of the cavity.

17 Claims, 17 Drawing Sheets

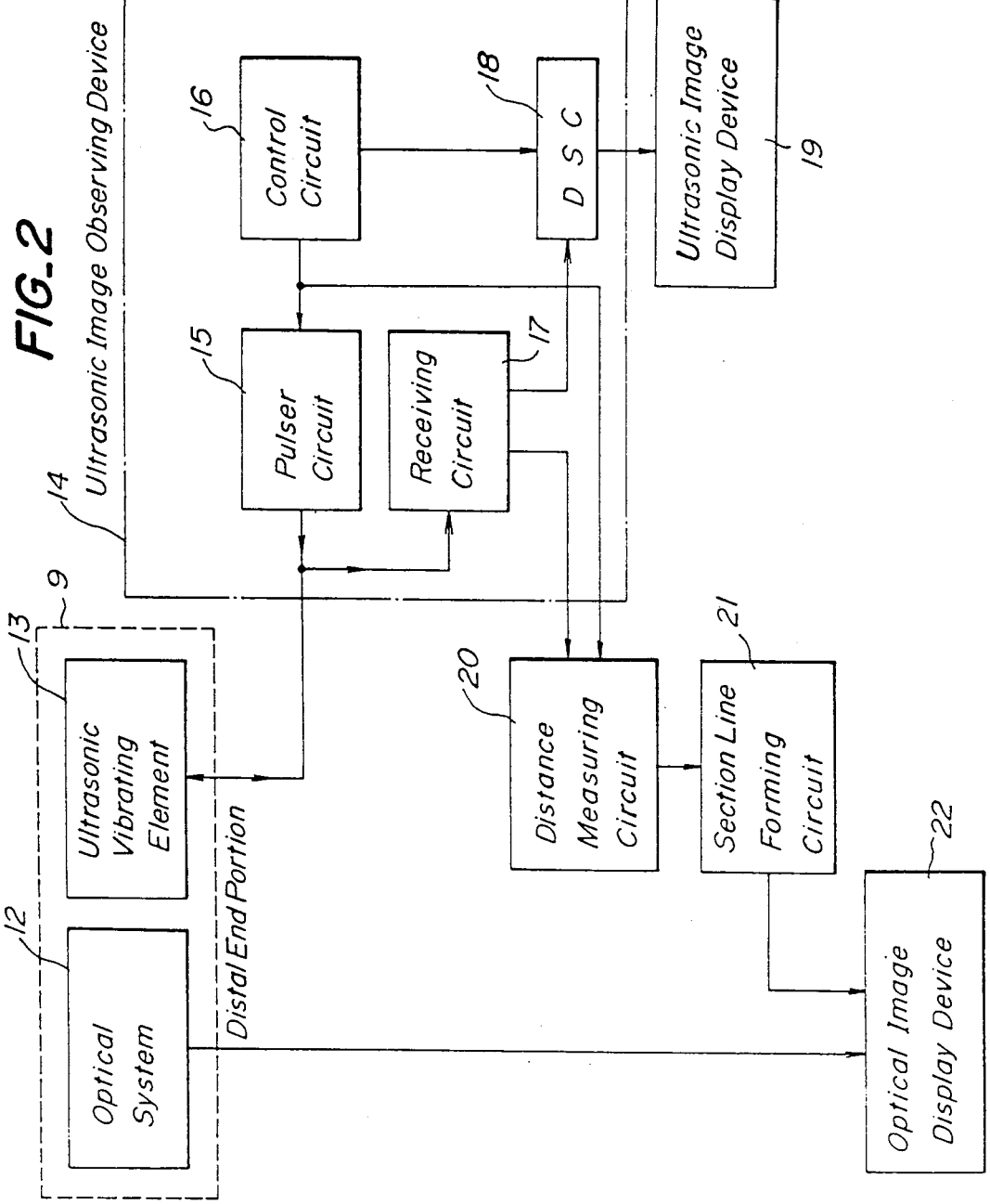

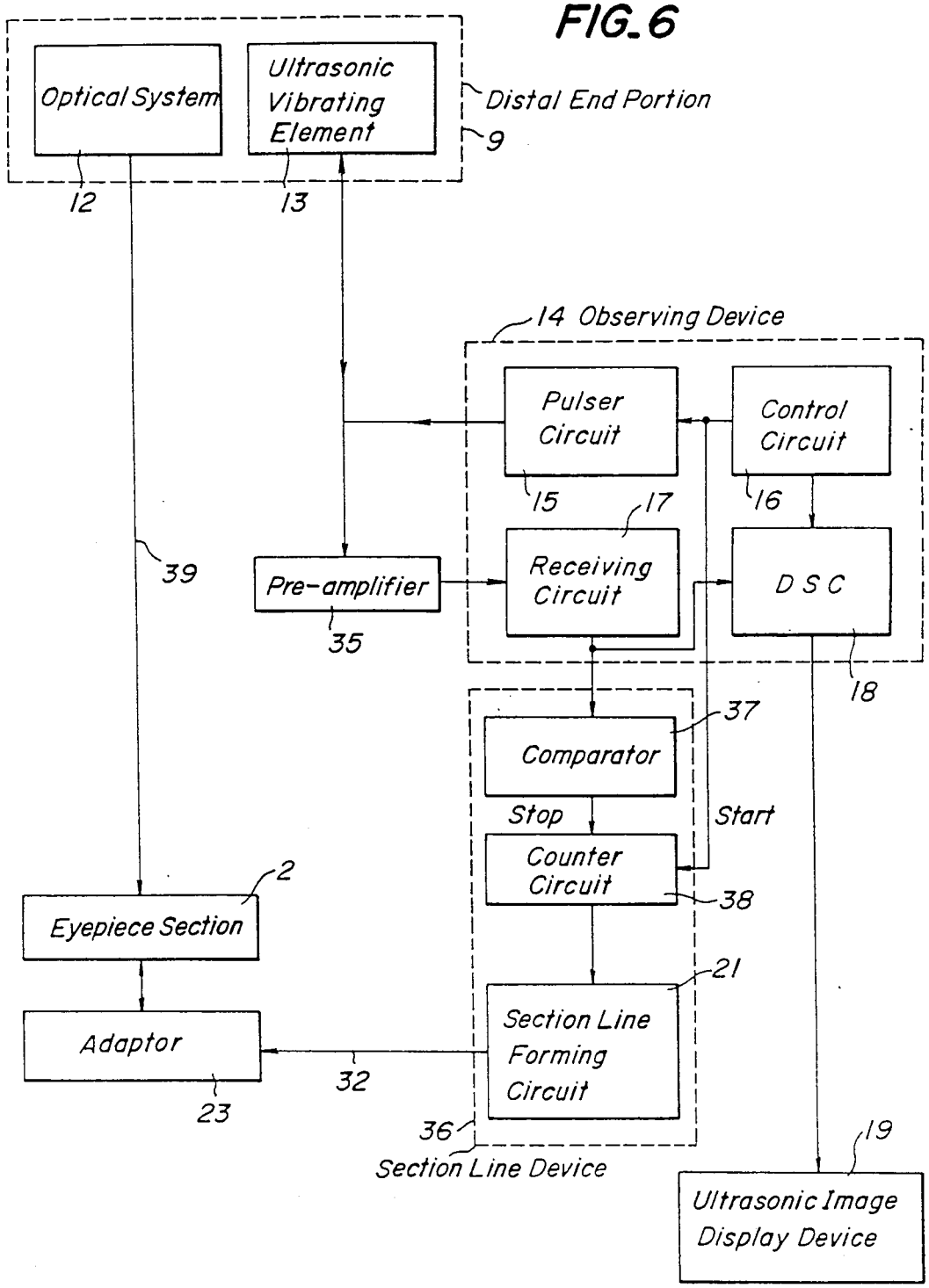

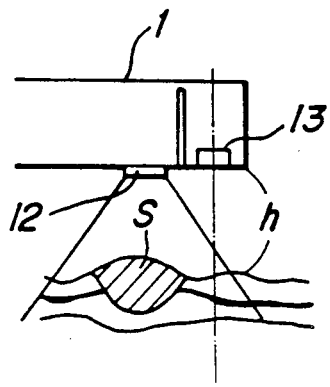
FIG._7A
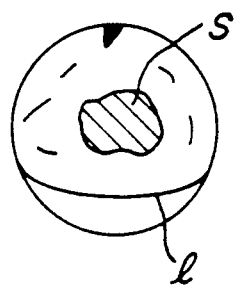
FIG._7B
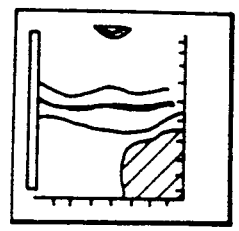
FIG._7C
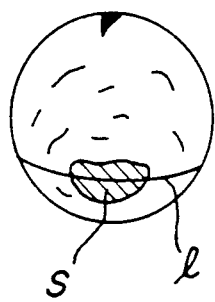
FIG._7D
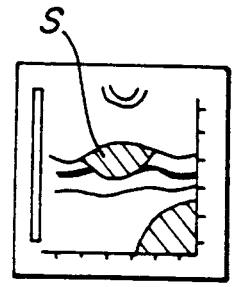
FIG._7E

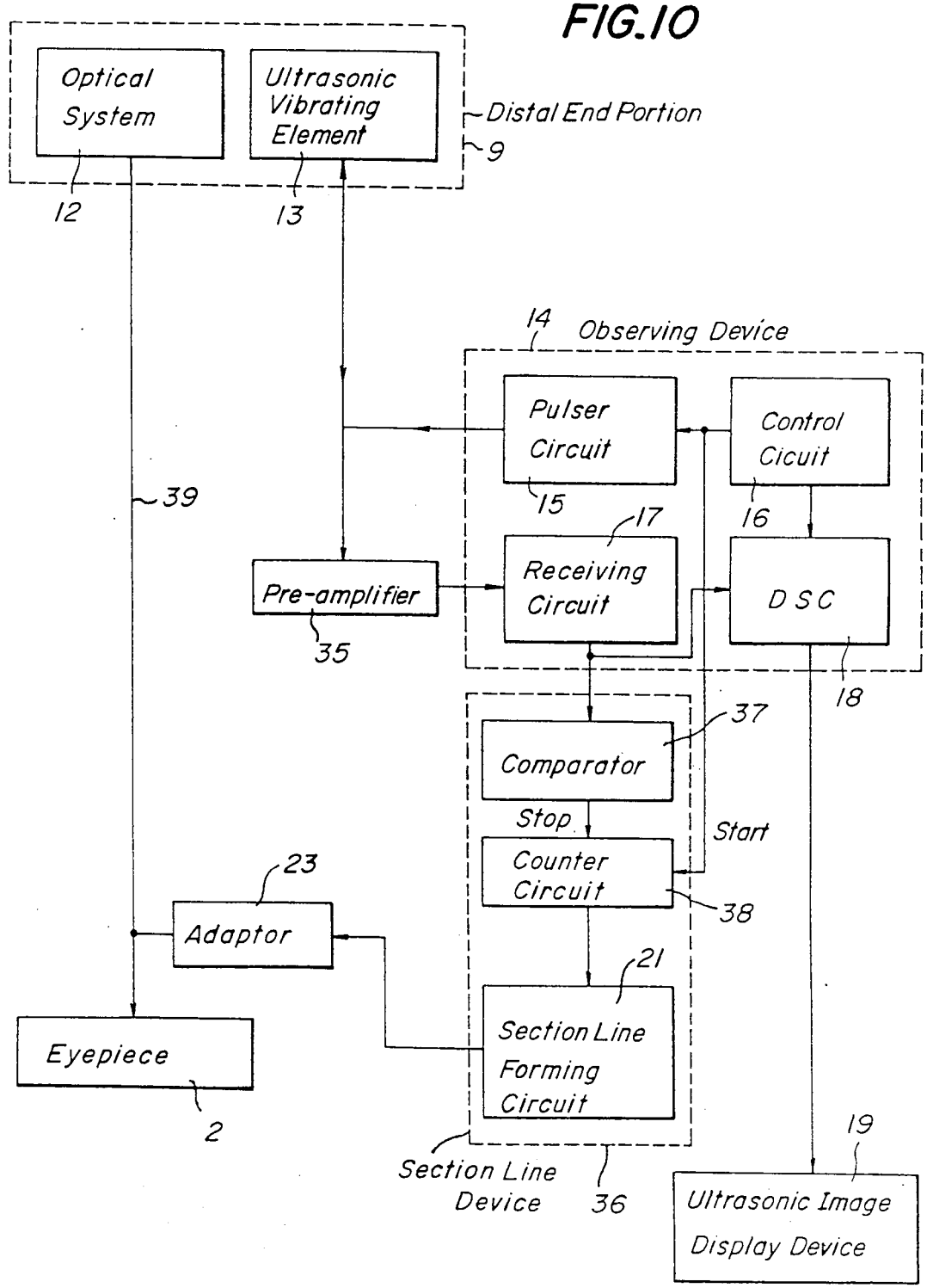

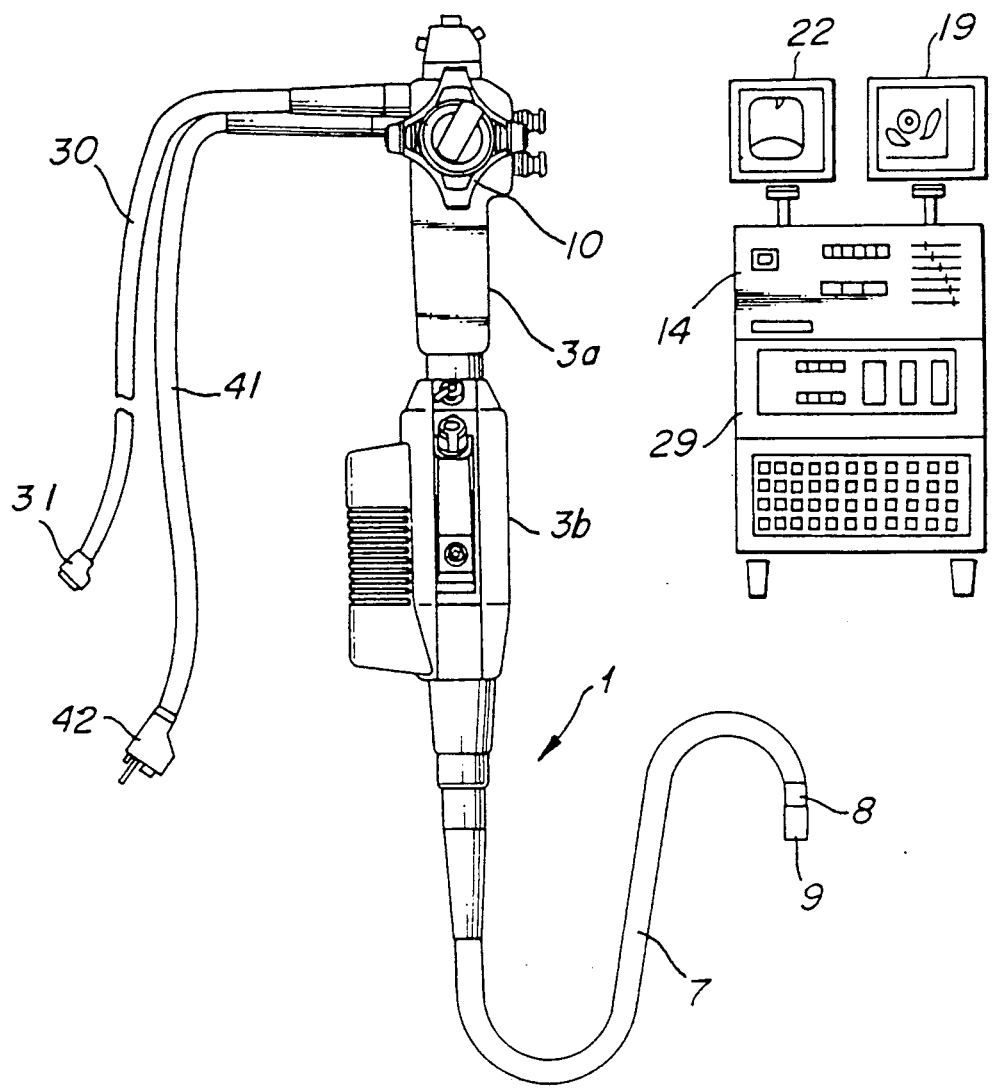

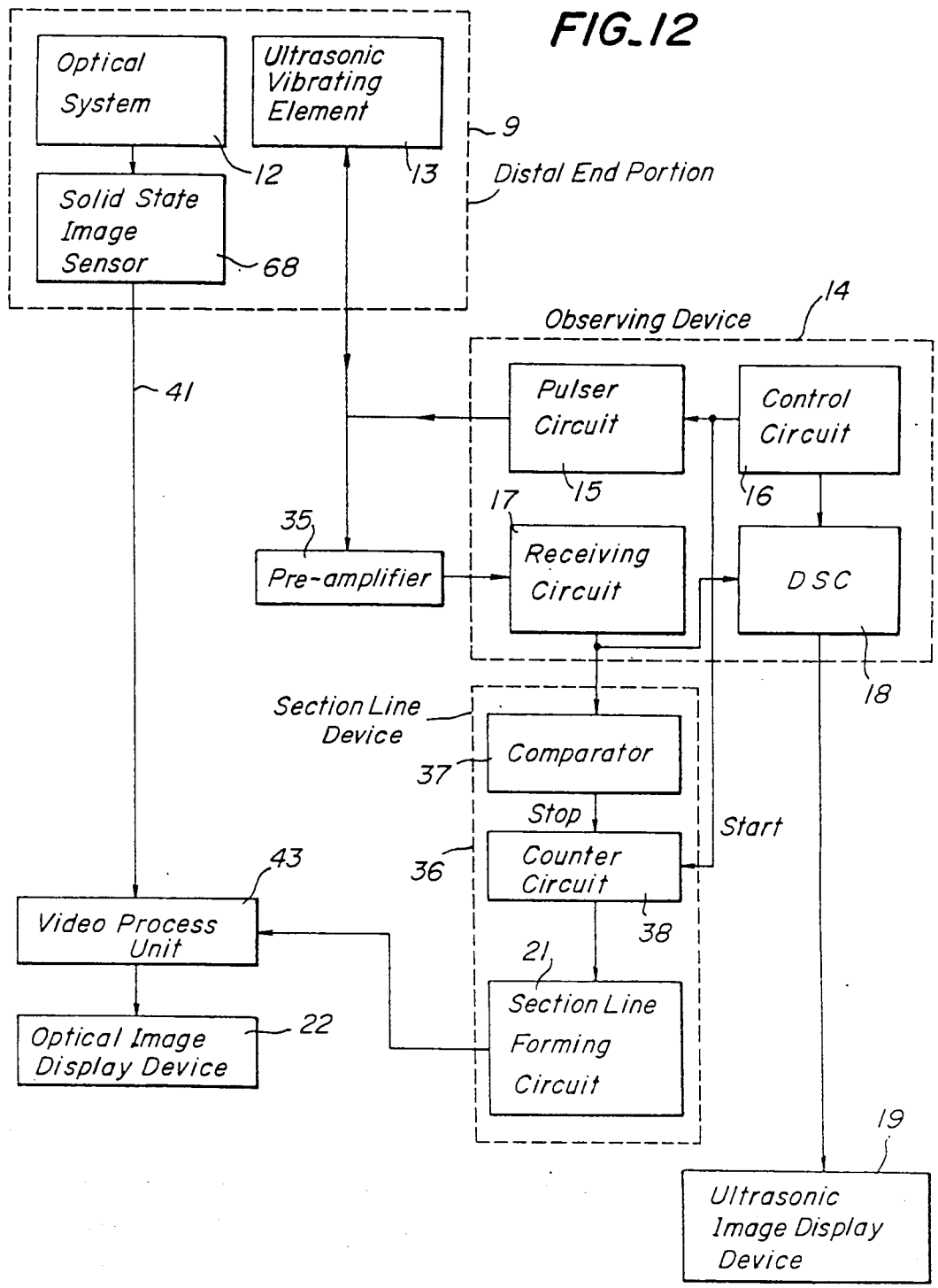
FIG_12

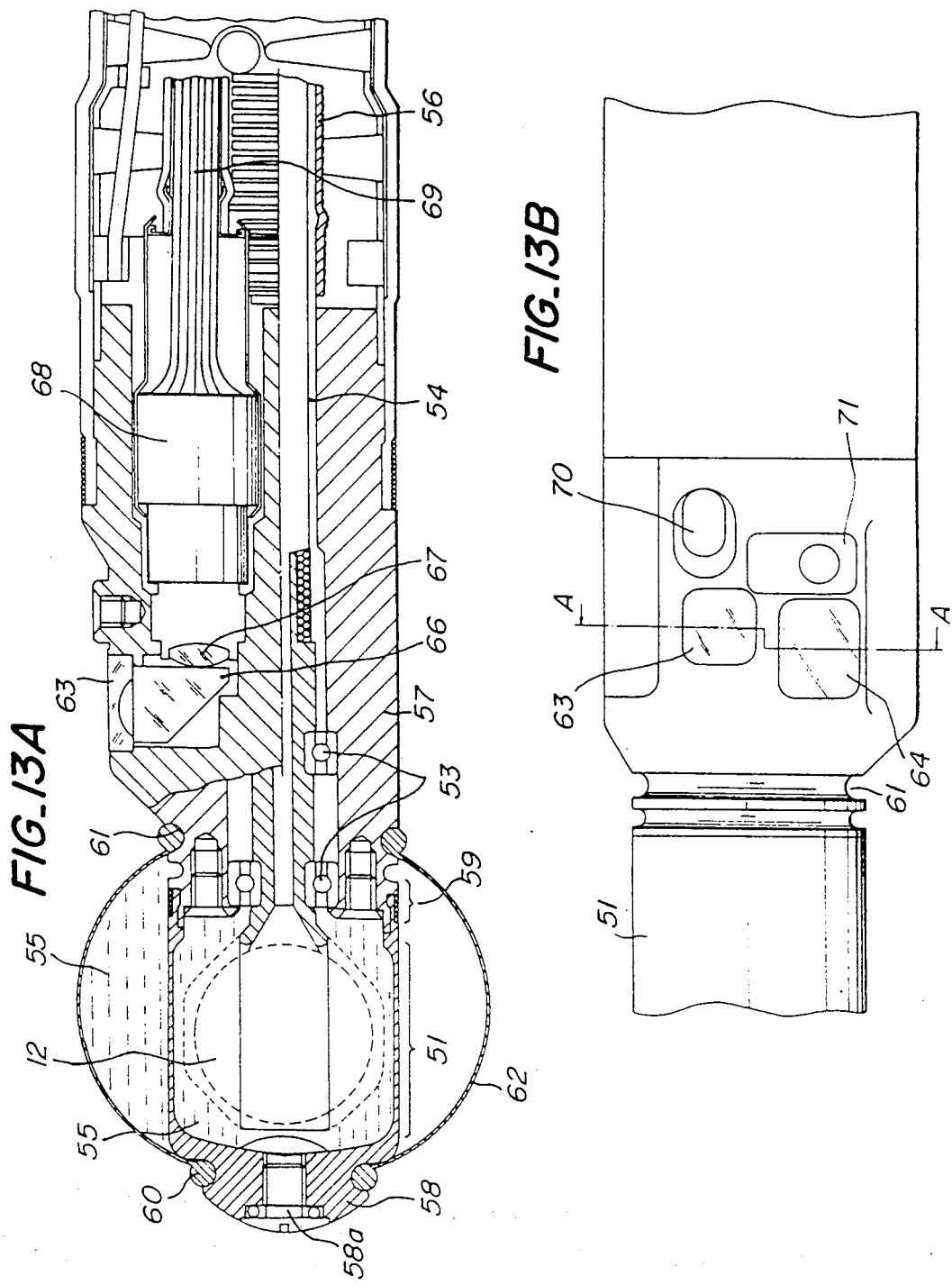

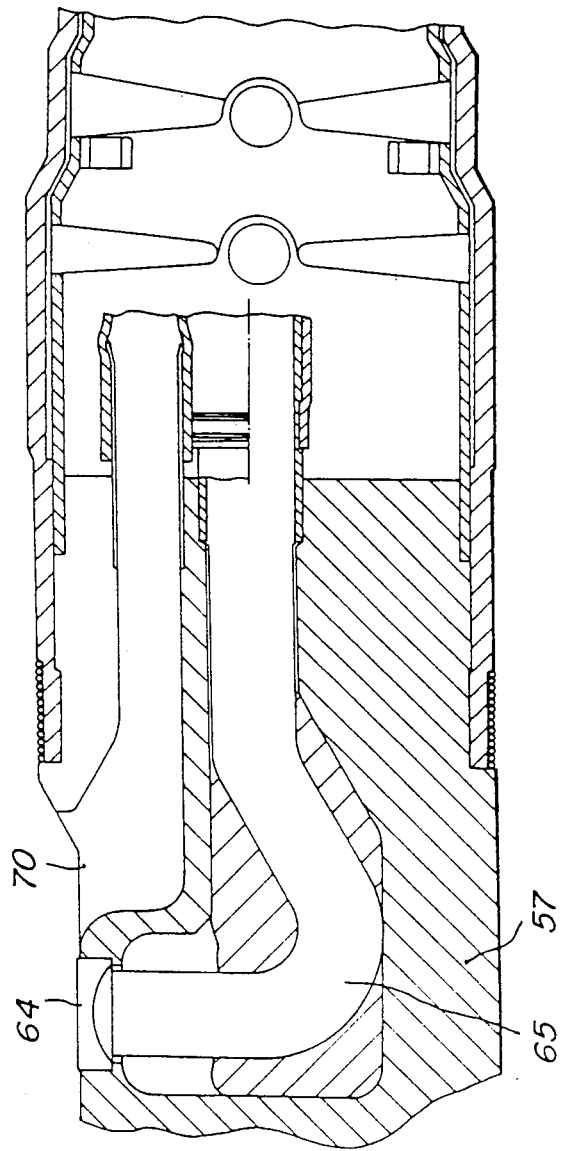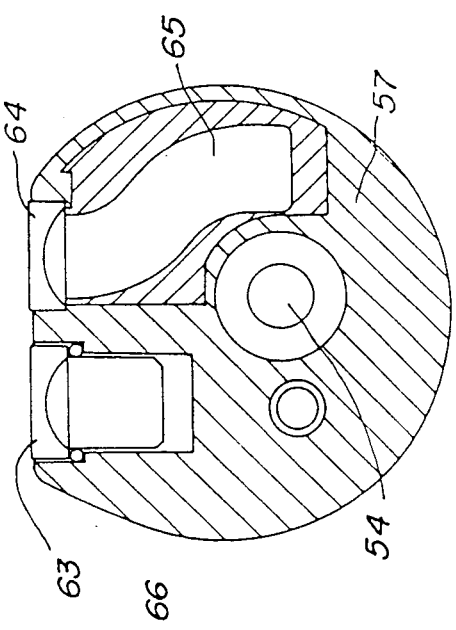
FIG.13C
FIG.13D

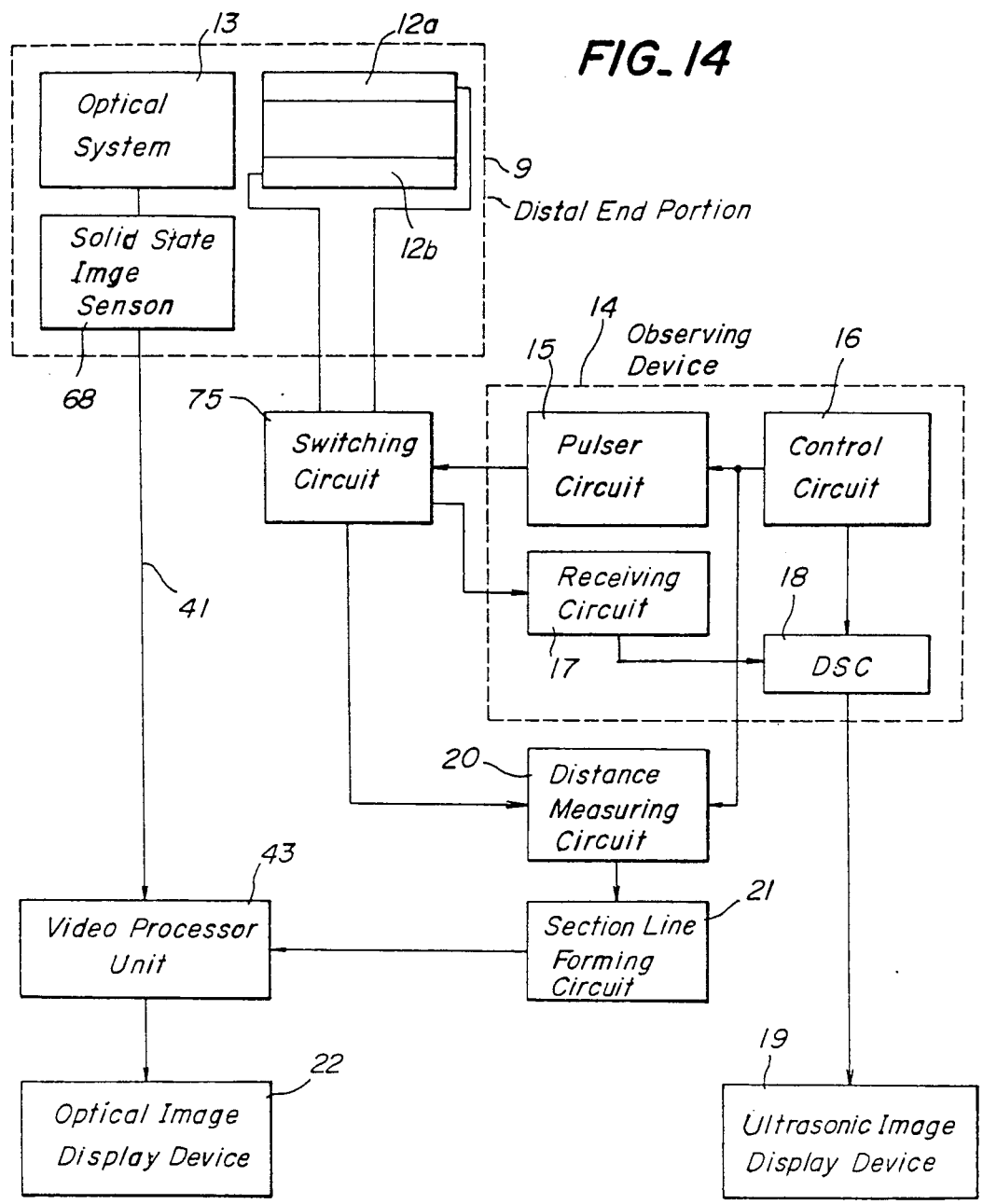

ULTRASONIC ENDOSCOPE APPARATUS

BACKGROUND OF THE INVENTION

1. Field of the Invention and Related Art Statement

The present invention relates to an ultrasonic endoscope apparatus comprising an endoscope having an insertion section which is insertable into a body under inspection, optical image observing means having an objective lens arranged in a distal end of the insertion section for forming an optical image of the body, and ultrasonic image observing means having an ultrasonic vibrating element provided in the distal end of the insertion section for forming an ultrasonic sectional image of the body.

The above mentioned ultrasonic endoscope apparatus for finding and diagonosing abnormal substances formed in a cavity wall of a living body, such as tumors formed on inner and outer walls of a stomach has been widely used. In such an ultrasonic endscope apparatus, the insertion section having the ultrasonic vibrating element installed in the distal end thereof is inserted into the cavity of the body, and a space between the distal end and the cavity wall is filled with an ultrasonic wave propagating medium, such as a physiological saline solution, by introducing the medium into a balloon arranged on the distal end of the insertion section. Then, the ultrasonic vibrating element is driven to effect the ultrasonic inspection. In this case, since a part of the cavity on which the ultrasonic wave is made incident could not be seen in the optical inspecting field of view, said part of the cavity could not be positively confirmed by the optical image, so that the ultrasonic image of the desired position of the cavity could not be obtained.

Japanese Utility Model Publication Kokai-shou 58-157,101 describes an ultrasonic endoscope apparatus in which a light emitting portion is provided at an end member of the insertion section. Upon using such an apparatus, a light beam emitted from the distal end of the insertion section is monitored from the outside of the body with the naked eye to confirm the direction in which the ultrasonic wave is emitted. German Patent Laid-open Publication p 33 36 803, discloses another known ultrasonic endoscope apparatus in which a light emitting element is provided on the ultrasonic probe and an emitted light beam is monitored by means of an endoscope inserted into a cavity of the body which is different from the cavity which is inspected by the ultrasonic endoscope apparatus. In these known ultrasonic endcope systems, the portion of the cavity which is inspected by the ultrasonic image is confirmed by monitoring the light beam which has passed through cavity walls or organs of the body.

Japanese Patent Publication Kokai-shou 58-133,232, describes a further known ultrasonic endoscope apparatus in which an image pick-up element and an ultrasonic vibrating element are mounted on the same rotating member so that the optical image and ultrasonic image always have a predetermined positional relationship. In such apparatus, after a position of the cavity has been confirmed by the optical image, the ultrasonic image may be obtained.

In the known ultrasonic endoscope systems described in Japanese Utility Model Publication Kokai-shou 58-157,101 and German Patent Publication P 33 36 803, the light beam could not be directly monitored, but is detected via the body. The position of the cavity on which the ultrasonic wave is made incident could not be determined precisely, and it is sometimes impossible to monitor the light beam at all depending upon the portion to be inspected.

In the known apparatus disclosed in Japanese Patent Publication Kokai-shou 58-133,232, since the ultrasonic vibrating element and image pick-up element are provided on opposite surfaces of the rotating member, it is impossible to monitor the optical image when the ultrasonic sectional image is monitored. Further, since it is required that the plane of the ultrasonic sectional image and the optical axis coincide with each other, this solution could not be applied to an endoscope having an inclined viewing axis.

Japanese Patent Publication Kokai-shou 63-3,616, discloses a further known ultrasonic endoscope apparatus in which a reflecting mirror is rotated and a light beam is emitted in synchronism with the rotation of the mirror to detect the part of the cavity under ultrasonic inspection. However, in this known apparatus the construction of the distal end of the insertion section tends to be complicated and the diameter of the insertion section is large.

SUMMARY OF THE INVENTION

The present invention has for its object to provide a novel and useful ultrasonic endoscope apparatus which can avoid the above explained drawbacks of the known systems, so that a section line indicating the plane of the ultrasonic sectional image can be displayed accurately during a scanning procedure for obtaining the ultrasonic sectional image.

According to the invention, an ultrasonic endoscope apparatus comprises:

an endoscope having an insertion section to be insertable into a cavity of body under inspection;

an optical image inspecting means having an objective lens installed in a distal end of the insertion section for forming an optical image of the cavity;

an ultrasonic image inspecting means having an ultrasonic vibrating element arranged in the distal end of insertion section for forming an ultrasonic sectional image of the cavity; and a displaying means for displaying an image of a line along which the ultrasonic sectional image is formed on the optical image of the cavity formed by said optical image inspecting means in the superimposed manner.

BRIEF DESCRIPTION OF THE DRAWINGS

FIG. 2 is a block diagram of the apparatus illustrated in FIG. 1;

FIG. 6 is a block diagram of the apparatus illustrated in FIG. 5;

FIGS. 7A to 7E represent several embodiments of the superimposed image;

FIG. 10 is a block diagram showing the construction of the apparatus shown in FIG. 9;

FIGS. 11A and 11B show a fifth embodiment of the ultrasonic endoscope apparatus according to the invention;

FIG. 12 is a block diagram of the apparatus illustrated in FIG. 11;

FIGS. 13A to 13D show the detailed construction of the distal end of the insertion section of the apparatus according to the invention; and FIG. 14 is a block diagram of a sixth embodiment of the ultrasonic endoscope apparatus according to the invention.

DESCRIPTION OF THE PREFERRED EMBODIMENT

Figure 1:
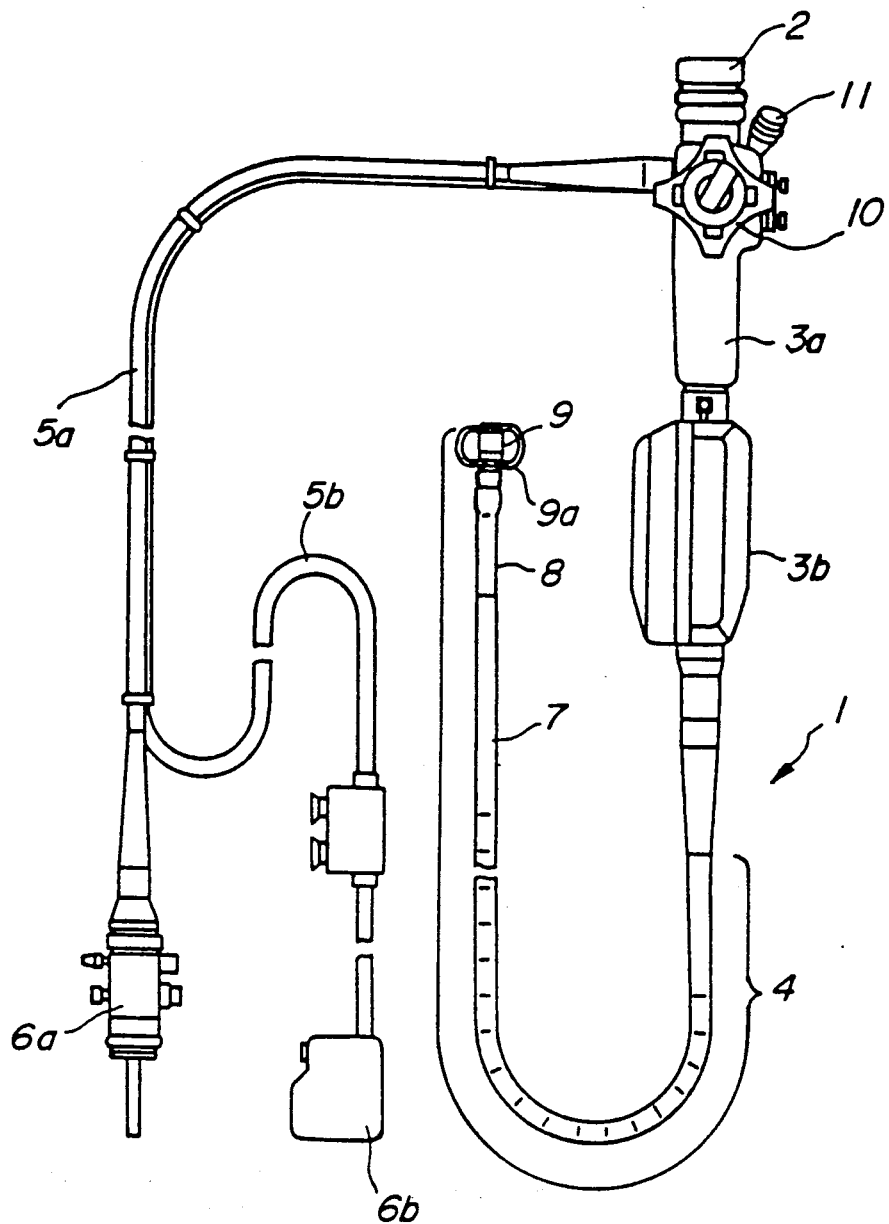
FIG. 1 is a perspective view showing the overall construction of a first embodiment of the ultrasonic endoscope apparatus according to the invention.

FIG. 1 is a perspective view showing the construction of the endoscope of a first embodiment of the ultrasonic endoscope apparatus according to the present invention. The endoscope 1 comprises an eyepiece section 2, a main operating section 3a, a sub-operating section 3b, an insertion section 4, a universal cable 5a, an electric signal cable 5b, a connector 6a connected to the universal cable 5a, and a connector 6b coupled with the electrical signal cable 5b. The insertion section 4 comprises a flexible portion 7, a bending portion 8 and a distal end portion 9 on which a balloon 9a is secured. Within the insertion section 4 there are extended image guide, light guide, forceps channel, etc. On the main operating section 3a there are provided an angle nob 10 and an inlet 11 for forceps. By suitably operating the angle nob 10, the bending portion 8 of the insertion section 4 may be bent so that the end portion 9 may be oriented into any desired direction. A forceps may be inserted into the channel from the inlet 11 and a piece of a body under inspection may be picked and collected. The incident end of the light guide is projected from the connector 6a and may be optically coupled with a light source unit not shown. By conducting light emitted by the light source unit via the light guide within the body cavity under inspection, a part of the cavity may be illuminated. An image of the illuminated part of the cavity may be observed by means of an objective lens provided in the distal end of the insertion section 4, image guide and eyepiece section 2.

It should be noted that the optical image of the cavity may be observed by using a solid state image pick-up installed in the distal end of the insertion section or on the eyepiece section 2 as will be explained hereinlater.

FIG. 2 is a block diagram showing the construction of the apparatus shown in FIG. 1. The distal end portion 9 includes an optical system 12 including the objective lens and an ultrasonic vibrating element 13. The ultrasonic vibrating element 13 is driven by an ultrasonic image observing device 14 having pulser circuit 15, control circuit 16, receiving circuit 17 and DSC (digital scan converter) 18.

When the ultrasonic vibrating element 13 is energized by the pulser circuit 15 via the control circuit 16, the element emits an ultrasonic wave which is made incident upon the body to be inspected. A part of the ultrasonic wave is reflected by the body and the reflected ultrasonic echo is received by the ultrasonic vibrating element 13. The ultrasonic signal (reflected echo signal) thus obtained is received by the receiving circuit 17, is processed by the DSC 18, and then is converted into the ultrasonic sectional image signal. The thus obtained ultrasonic image signal is supplied to an ultrasonic image display device 19 such as a television monitor. In this manner, the ultrasonic sectional image of the cavity can be displayed on the display device 19.

According to the present invention, there is arranged a distance measuring circuit 20 connected to the receiving circuit 17 as well as to the control circuit 16, so that when the control circuit supplies the signal to the pulser circuit 15, the signal is also supplied to the distance measuring circuit 20. Then, the distance measuring circuit 20 detects the distance from the ultrasonic vibrating element 13 to the surface of the cavity under inspection. The method of detecting the distance will be explained in detail hereinbelow. The thus detected distance information is supplied to a section line forming circuit 21 which forms image information representing the locus of the section line in the optical image of the cavity. The image information thus formed is then supplied to an optical image display device 22. To the optical image display device 22 is also supplied the optical image from the optical system 12. In this manner, the section line image of the ultrasonic image can be displayed on the optical image display device 22 in a superimposed manner with the optical image.

Now the method of forming the section line will be explained. The distance between the optical system 12 and the surface of the cavity under inspection is first detected in accordance with the known method by utilizing the ultrasonic echo signal, and then the section line is formed on the basis of the measured distance. In order to detect the distance, the distance measuring circuit 20 is actuated when the control circuit 16 sends the signal to the pulser circuit 15, and the echo signal reflected from the surface of the cavity is received by the receiving circuit 17 to detect the first echo signal which is supplied to the distance measuring circuit 20. The distance measuring circuit 20 measures the distance by detecting the time period from the time instant at which the ultrasonic wave is emitted from the ultrasonic vibrating element 13 to the time instant at which the first echo signal is detected.

Figure 3A:
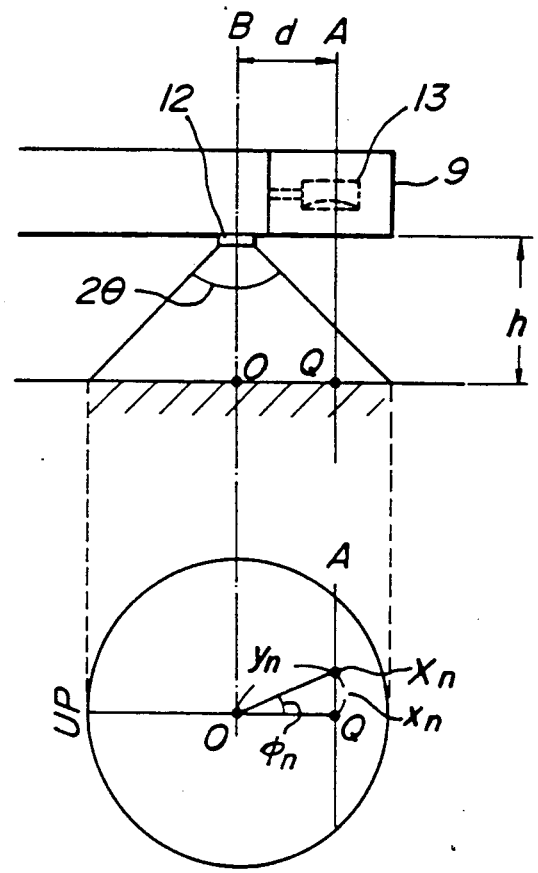
FIGS. 3A and 3B are diagrams depicting the principle of forming the section line in the optical image according to the present invention.
Figure 3B:
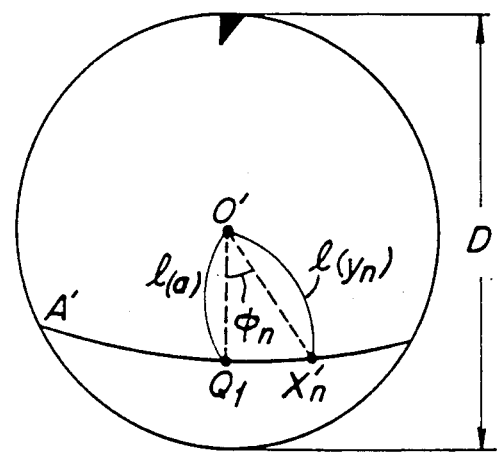

FIGS. 3A and 3B show the principle of forming the section line according to the invention. As shown in FIG. 3A, the section line on the ultrasonic image is denoted by A and this section line is perpendicular to the insertion direction of the insertion section of the endoscope. The optical system 12 provided at the distal end portion of the insertion section is of the inclined observation type and has an angle of view of $2\theta$. The ultrasonic vibrating element 13 is provided at a position which is far remote from the proximal end with respect to the optical system 12. A center B of the field of view of the optical system 12 is parallel to the section line A, but is separated therefrom by a distance d. A circle described in a lower part of the drawing of FIG. 3A denotes the field of view of the optical system 12 on the surface of the cavity under inspection. On the optical image display device 22 there is displayed a substantially circular image having the diameter D as shown in FIG. 3B.

The section line A is represented as a group of points $x_n$ denoted by a distance $y_n$ between the center of the field of view and the point on the cavity surface on which the ultrasonic wave is made incident, and an angle $\phi_n$ with respect to the insertion direction.

Figure 4:
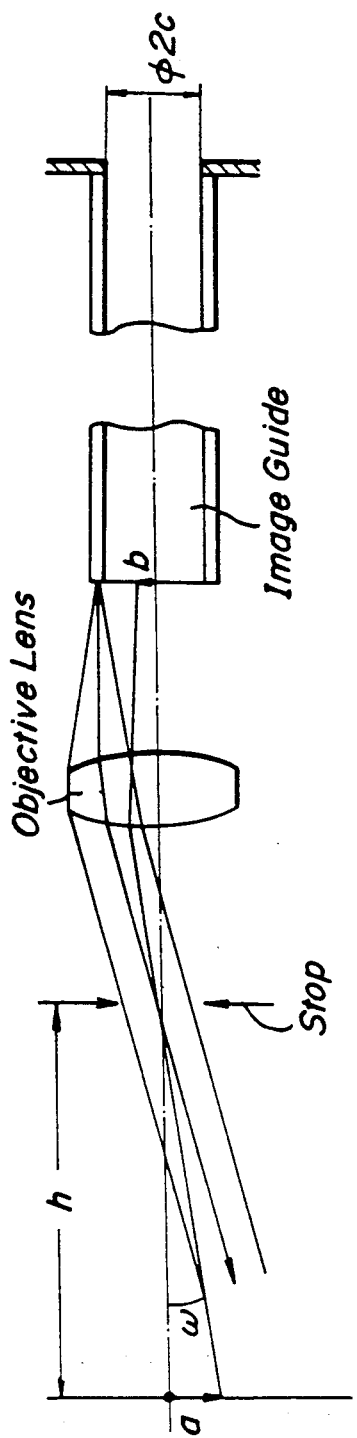
FIG. 4 is a diagram showing the principle of forming the section line.

In the optical system 12 for use in the endoscope, the following relationships are satisfied when the angle of view is smaller than 90 degrees as shown in FIG. 4.

$$c = f \sin\theta \tag{1}$$

$$b = f \sin\omega \tag{2}$$

wherein f is a focal length of the objective lens, $2\theta$ is the angle of view, 2c is a diameter of a mask of the image guide and b is a height of the image on the image guide. From the above equations (1) and (2), the height of the image on the image guide of an object which has the height a and is positioned at a point remote from the focal point of the objective lens by a distance h may be expressed by the following equation.

$$b = \frac{c}{\sin\theta} \sin\left(\tan^{-1}\frac{a}{h}\right) \tag{3}$$

Therefore, the object in the field of view having the diameter D on the optical image display device 22 may be represented by a group of points $X'_n$ ($l(y_n)$, $\phi_n$), wherein $$l(y_n) = \frac{D}{2\sin\theta} \sin\left(\tan^{-1}\frac{y_n}{h}\right) \tag{4}$$

wherein $$y_n = \sqrt{a^2 + b^2} \tag{5}$$

$$\phi_n = \tan^{-1}\frac{x_n}{a}$$

In the present embodiment, the distance h is detected by utilizing the ultrasonic wave and the locus of the section line is calculated from the equations (1) and (2). The image data representing the section line thus obtained is supplied to the optical image display device 22 and the section line is displayed thereon in the superimposed manner with the optical image. Therefore, the operator can confirm accurately and easily the section on which the ultrasonic sectional image is taken by monitoring the optical image display device. As will be explained hereinafter, in case of obtaining the ultrasonic image, the balloon is inflated by introducing the ultrasonic wave propagating medium therein so that the cavity surface is flattened, and therefore it is sufficient to measure the distance only at one point. Further, the distance between the ultrasonic vibrating element 13 and the object side focal point of the objective lens may be taken into account in measuring the distance.

Figure 5A:
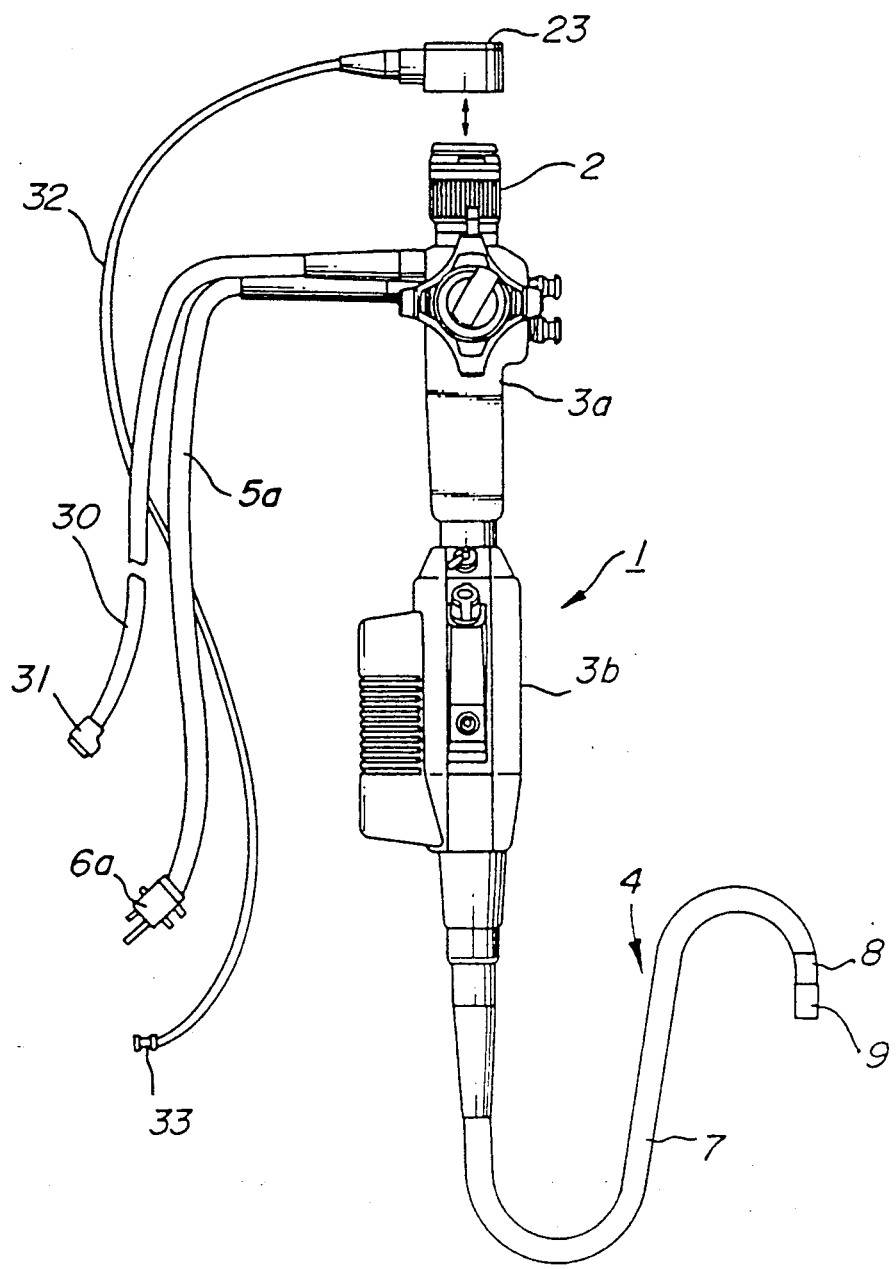
FIGS. 5A, 5B and 5C show a second embodiment of the ultrasonic endoscope apparatus according to the invention.
Figure 5B:
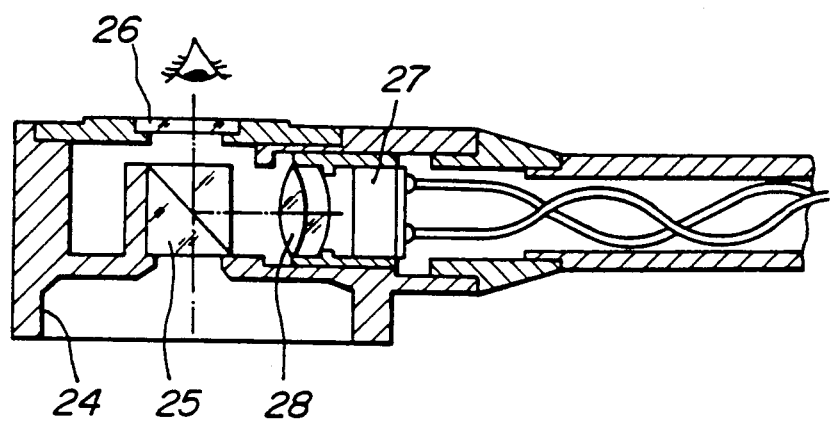
Figure 5C:
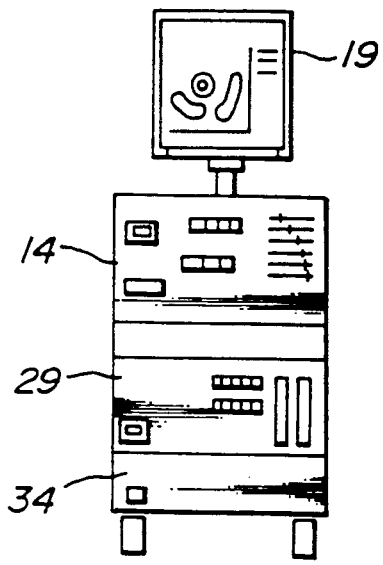

FIG. 5 is a perspective view illustrating a second embodiment of the ultrasonic endoscope apparatus according to the present invention. In this embodiment, the image of the section line of the ultrasonic image is displayed on the observing section of the endoscope. In FIG. 5, portions similar to those shown in FIG. 1 are denoted by the same reference numerals used in FIG. 1. As shown in FIG. 5A, an adaptor 23 is detachably arranged on the eyepiece section 2 of the endoscope 1 and the section line is displayed in the adaptor. FIG. 5B is a cross section showing the detailed construction of the adaptor 23 on an enlarged scale. The adaptor 23 comprises a coupling member 24 for detachably coupling the adaptor to the eyepiece section 2, a half mirror 25 arranged at an upper portion of the coupling member, and a viewing glass plate 26 arranged above the half mirror. The optical image of the cavity picked-up by the objective lens in the optical system 12 and transmitted through the image guide can be directly monitored through the half mirror 25 and glass plate 26. In the coupling member 24 there is further arranged a liquid crystal display device 27 on which the section line of the ultrasonic image is displayed. The image of the section line displayed on the display device 27 can be seen by means of a lens 28 through the half mirror 25 and glass plate 26. Therefore, the operator can monitor the image of the section line and the optical image of the cavity in the superimposed manner. FIG. 5C shows a light source unit 29 to which the universal cable 5a is coupled via the connector 6a, an ultrasonic image observing device 14 to which a signal cable 30 connected to the ultrasonic vibrating element 13 is coupled by means of a connector 31, and a section line forming device 34 to which the adaptor 23 is coupled via signal cable 32 and connector 33.

FIG. 6 is a block diagram showing the whole construction of the apparatus of the second embodiment of the apparatus according to the invention. Only points which are different from the first embodiment will be explained. The echo signal detected by the ultrasonic vibrating element 13 is supplied to the receiving circuit 17 via a pre-amplifier 35. The ultrasonic image observing device 14 is connected to a section line device 36 which comprises comparator circuit 37, counter circuit 38 and section line forming circuit 21. The optical image of the cavity under inspection is picked-up by the optical system 12 provided at the distal end of the insertion section and is transmitted to the eyepiece section 2 by means of the image guide 39. As explained above, the adaptor 23 is detachably coupled with the eyepiece section 2. The adaptor 23 is connected to the section line forming device 21 by means of the signal cable 32 and connector 33. In the section line device 36, the echo reflected by the cavity is processed to measure the distance h to the cavity surface. That is to say, when the signal is supplied from the control circuit 16 to the pulser circuit 15, the start signal is supplied to the counter circuit 38 to initiate the counting of clock pulses having a constant frequency. During the counting operation, the comparator circuit 37 compares the echo signal received by the receiving circuit 17 with a predetermined reference value to detect the first echo from the surface of the cavity. When the first echo signal is detected, the comparator circuit 37 supplies the count stop signal to the counting circuit 38 to stop the counting operation. In this manner, the counter has counted the number of clock pulses which have been supplied to the counter during a time interval from a time at which the ultrasonic wave was emitted to a time at which the first echo was detected. Since the propagating speed of the ultrasonic wave in the medium is known, the distance h can be calculated from the count value. In the section line forming circuit 21, the image data representing the section line is derived in accordance with the equations (4) and (5), and the thus derived image data is supplied to the adaptor 23. In the adaptor 23, the section line is displayed on the liquid crystal display device 27 in accordance with the image data of the section line. The section line image on the display device 27 can be observed together with the optical image of the cavity by means of the lens 28, half mirror 25 and glass plate 26.

Now the actual inspection with the aid of the ultrasonic endoscope apparatus according to the invention will be explained with reference to FIG. 7. The insertion section of the endscope is first inserted into the cavity up to a desired portion of the cavity. Then the optical image of the cavity is monitored as illustrated in FIG. 7A. In this case, in the optical image displaying device 22 there can be seen the optical image of the surface of the cavity in which a humor S is positioned substantially at the center of the field of view as shown in FIG. 7B. In this condition, the ultrasonic wave is emitted from the ultrasonic vibrating element 13 toward the cavity wall, and the distance h is measured by utilizing the reflected echo. The section line 1 is derived in accordance with the principle explained above and is displayed in the superimposed manner with the optical image of the cavity surface as depicted in FIG. 7B. As shown in FIG. 7B since the section line 1 does not pass through the tumor S, on the ultrasonic image display device 19 there is displayed the ultrasonic sectional image of the cavity which is deviated from the tumor S as shown in FIG. 7C.

Then, the operator handles the insertion section of the endoscope such that the section line 1 passes through the tumor S as shown in FIG. 7D. Then, the ultrasonic image cut along the tumor S is displayed on the ultrasonic image display device 19 as illustrated in FIG. 7E. In this manner, by using the apparatus according to the invention, it is possible to effect the ultrasonic scanning by visually monitoring a part of the cavity at which the ultrasonic sectional image is formed, so that the ultrasonic image of the tumor S can be accurately obtained.

In the second embodiment of the ultrasonic endoscope apparatus according to the invention, the sectional plane of the ultrasonic image is perpendicular to the inserting direction of the insertion section of the endoscope. However, the present invention is not limited to such an embodiment, and may be equally applied to an endoscope in which the sectional plane is parallel to the inserting direction as long as the section line is correctly displayed with respect to the optical image. Moreover, the method of scanning the ultrasonic wave is not limited to the radial scan, but may be electronic linear scan, electronic sector scan, electronic convex scan, etc.

Figure 8A:
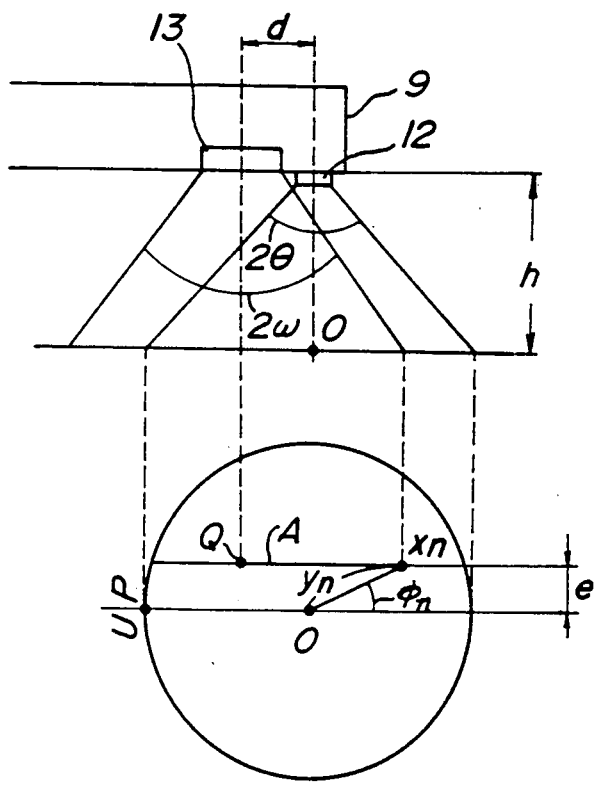
FIGS. 8A and 8B show the principle for forming the section line in a third embodiment of the ultrasonic endoscope apparatus according to the invention.
Figure 8B:
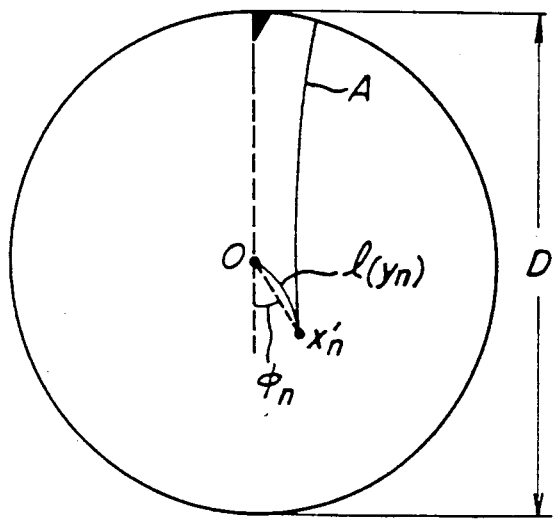

FIG. 8 shows the principle of forming the section line in the third embodiment of the apparatus according to the invention. In the present embodiment, the ultrasonic scan is effected in a direction which is parallel to the inserting direction of the insertion section of the endoscope. The section line A may be expressed by a series of points $X_n$ represented by the distance $y_n$ from the center of the field of view and the angle $\phi_n$ on the actual surface of the body under inspection. Therefore, on the display screen, the section line may be represented by a series of points $X'_n(l(y_n), \phi_n)$ in the field of view having the diameter of D, wherein $$y_n = \sqrt{(d - h\tan\omega)^2 - e^2} \quad (6)$$

$$\phi_n = \tan^{-1} \frac{e}{h\tan\omega - d} \quad (7)$$

In the above equations, d is a distance from the center of the field of view to the observing center of the ultrasonic vibrating element 13, and e is a distance from the sectional plane of the ultrasonic image to a plane which passes through the center of the field of view and is parallel to the inserting direction.

Figure 9A:
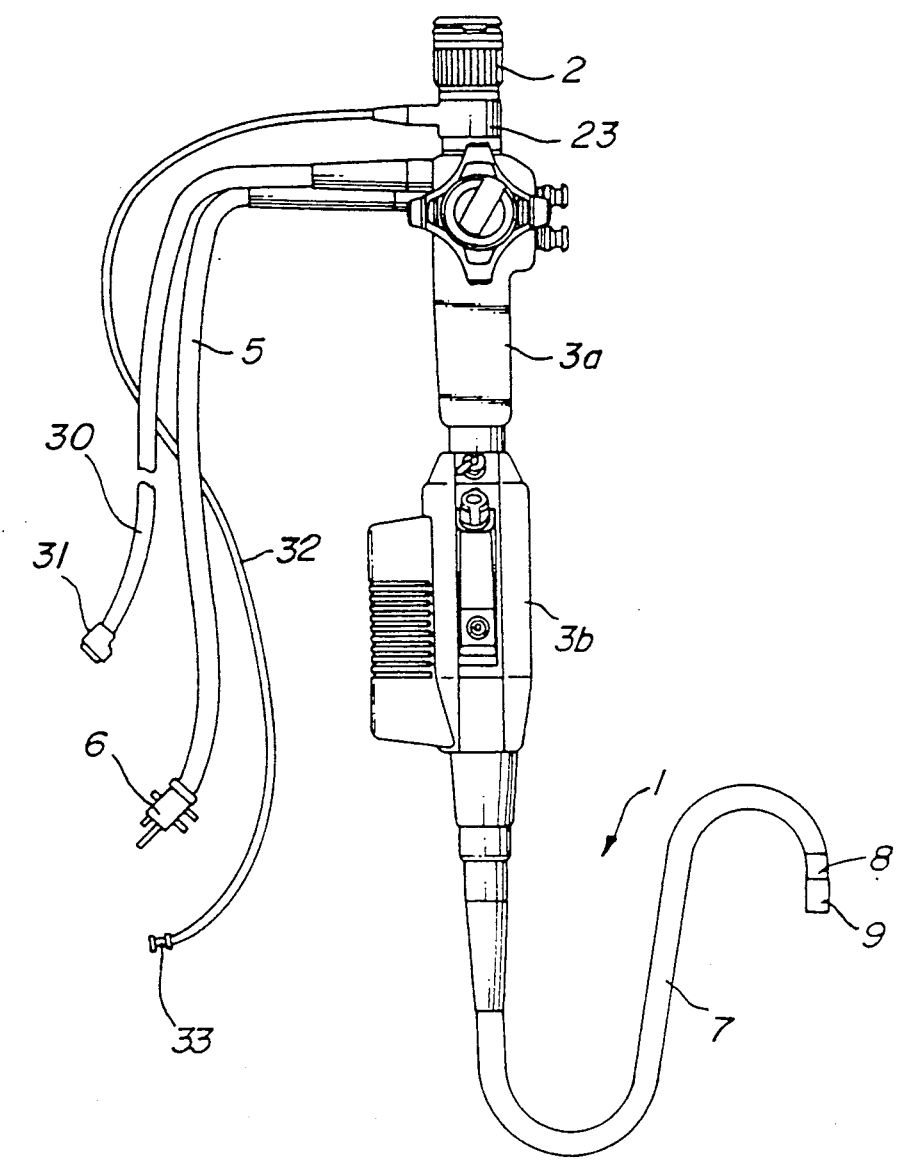
FIGS. 9A and 9B illustrate a fourth embodiment of the ultrasonic endoscope apparatus according to the invention.
Figure 9B:
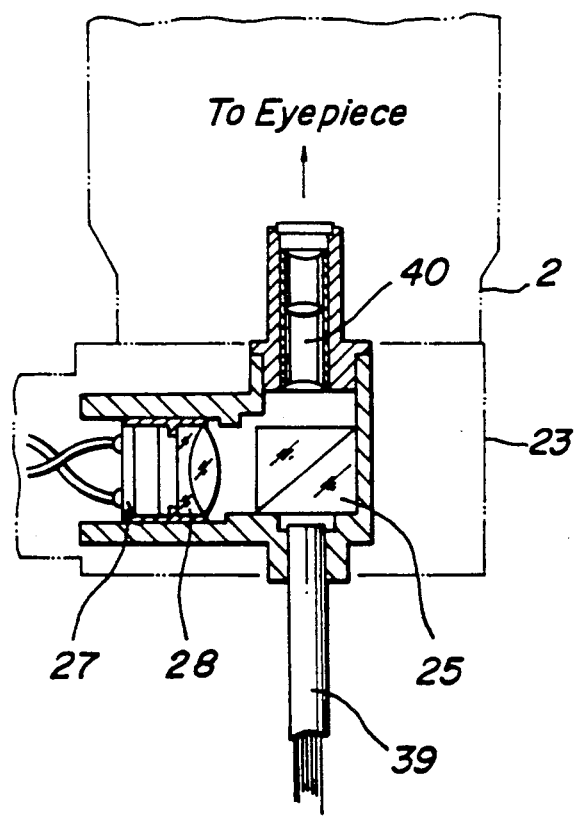

FIG. 9 shows the fourth embodiment of the ultrasonic endoscope apparatus according to the invention. The present embodiment is similar to the second embodiment shown in FIG. 5, so that portions similar to those shown FIG. 5 are represented by the same reference numerals of FIG. 5. As illustrated in FIG. 9A, the section line display device is formed as an adaptor 23 which can be detachably inserted between the eyepiece section 2 and the main operating section 3a of the endoscope 1. FIG. 9B depicts the detailed construction of the adaptor 23. The optical image picked-up by the optical system provided in the distal end of the endscope is transmitted via the image guide 39 and can be observed by means of the half mirror 25 and relay lens 40. The liquid crystal display device 27 is provided in the adaptor 23 and the image of the section line displayed on the display device 27 can be monitored by means of the projection lens 28, half mirror 25 and relay lens 40. In this manner, the section line and the optical image can be monitored via the eyepiece section 2 in the superimposed manner.

FIG. 10 is a block diagram showing the construction of the apparatus of the fourth embodiment. In the present embodiment the liquid crystal display device 27 of the adaptor 23 is connected to the section line forming circuit 21 provided in the section line device 36. The remaining construction is same as the third embodiment illustrated in FIG. 6.

FIGS. 11, 12 and 13 show the outer appearance, block diagram and detailed construction of the distal end of the fifth embodiment of the ultrasonic endoscope apparatus according to the invention. In the present embodiment, the optical image of the cavity wall formed by the optical system 12 is picked-up by a solid state image sensor such as CCD to generate the image signal which is then supplied by means of cable 41 including the light guide and electric signal wires and connector 42 to a video processor unit 43. The image signal is then displayed on the display device in the optical image displaying device 22. The image data of the section line calculated from the measured distance h is supplied from the section line forming circuit 21 to the video processor unit 43 and is superimposed on the image signal of the picked-up optical image. Then, the superimposed image signals are displayed on the display screen of the optical image displaying device 22.

FIG. 13 shows the detailed construction of the distal end portion of the endscope of the present embodiment. FIG. 13A is the longitudinal cross section, FIG. 13B a side view, FIG. 13C a longitudinal cross section illustrating the light guide and FIG. 13D is a lateral cross section. The distal end portion 9 is connected to the sub-operating section 3b by means of the bending portion 8 and flexible portion 7. At the distal end portion 9 there is arranged an end sleeve 51 forming an ultrasonic observing window and the ultrasonic vibrating element 12 is rotatably arranged within the sleeve 51. A rotor 52 supporting the ultrasonic vibrating element 12 is journalled by bearings 53 and is coupled with a distal end of flexible shaft 54. The proximal end of flexible shaft 54 is extended up to the sub-operating section 3b and is connected to a motor provided therein, so that the ultrasonic vibrating element 12 can be rotated at a desired speed in the desired direction.

The end sleeve 51 constituting the ultrasonic transmitting and receiving window is filled with an ultrasonic wave propagating medium 55 such as liquid paraffin. The medium 55 is also existent between the flexible shaft 54 and a tube 56 surrounding the shaft. This contributes to lubricate the rotating shaft 54.

An end cap 58 is formed integrally with the sleeve 51 and a hole is formed in the end cap, said hole being clogged by a screw 58a. During the manufacture of the endoscope, the ultrasonic wave propagating medium 55 is introduced into the sleeve 51 through the hole. The end sleeve 51 is secured to a base member 57 of the distal end portion by means of a fitting portion 59. In the outer surface of the end cap 53 there is formed a ring-shaped recess 60 and in the outer surface of the base member 57 there is also formed a ring-shape recess 61, and a balloon 62 is detachably secured to the distal end portion by means of these recesses. The diameter of the recess 60 is smaller than that of the recess 61. Within the balloon 62 the ultrasonic wave propagating medium may be selectively introduced. That is to say, after the distal end of the endoscope has been inserted into a desired position in the cavity, the balloon 62 is inflated by introducing therein the ultrasonic wave propagating medium, so that the balloon is urged against the cavity wall. In this manner, the distal end of the endoscope can be stably fixed at a desired position within the cavity. After the observation is finished, the balloon 62 is shrunk by discharging the medium therefrom, so that the insertion section can be easily removed out of the cavity. In the present embodiment, since the front end of the insertion section is formed round, the insertion of the endoscope can be carried out easily.

To the base member 57 of the distal end portion 9 of the endoscope, there is secured the optical system. That is to say, a cover glass 63 for the observation and a cover glass 64 for the illumination ar arranged side by side in the outer surface of the base member 57. Under the cover glass 63 there are arranged a prism 66 for bending the optical path at right angles and an imaging lens 67 for forming the optical image of the cavity on the solid state image sensor 68. The outlet of the light guide 65 is arranged underneath the cover glass 64. The light guide 65 is extended to the main-operating portion 3a via the insertion section 7 while any undesired interference between the light guide and the flexible shaft is avoided. The light guide 65 is further extended up to the light source unit 14 by means of the cable 41 and connector 42. The solid state image sensor 67 is connected to a signal cable 69 which is extended to the main-operating section 3a via the insertion section 4 and is further extended to the video processor unit 42 by means of the cable 40 and connector 41.

As shown in FIG. 13B, a washing nozzle 70 is arranged near the cover glass 63 and further a suction inlet 71 is formed in the vicinity of the nozzle. These nozzle 70 and inlet 71 are extended to the main-operating section 3a via flexible protection tubes respectively.

FIG. 14 is a block diagram showing the sixth embodiment of the ultrasonic endoscope apparatus according to the invention. In the present embodiment, in the distal end portion 9 of the insertion section 4 of the endoscope 1 there are arranged two ultrasonic vibrating elements 12a and 12b in such a manner that their backs are faced with each other. In the operation, one of the elements 12a and 12b is used to form the ultrasonic sectional image, and the other is utilized to measure the distance for displaying the section line of the ultrasonic image in superimposition with the optical image of the cavity under inspection. These ultrasonic vibrating elements 12a and 12b may have the same characteristics, but it is preferable to constitute these elements to have different characteristics. Then, any one of the elements may be selectively utilized for the formation of the ultrasonic image in accordance with portions of the cavity and various diagnostic conditions. In the present embodiment, the first ultrasonic vibrating element 12a is used to obtain the ultrasonic sectional image and the second ultrasonic vibrating element 12b is used to measure the distance to the cavity wall surface. To this end, the first element 12a may be connectable to the pulser circuit 15 and receiving circuit 17 via a switching circuit 75 and the second element 12b is connectable to the pulser circuit 15 and distance measuring circuit 20 by means of the switching circuit 75. Similar to the first embodiment shown in FIG. 2, the pulser circuit 15 is driven by the control circuit 16 to generate the ultrasonic wave from the first ultrasonic vibrating element 12a, and the ultrasonic wave reflected from the cavity is received by the receiving circuit 17 to produce the echo signal. The echo signal is supplied to DSC 18 to derive the image signal, the image signal thus derived is supplied to the ultrasonic image displaying device 19 to display the ultrasonic sectional image. The oscillation signal generated by the pulser circuit 15 is also supplied to the distance measuring circuit 20 via the switching circuit 75 to measure the distance from the second ultrasonic vibrating element 12b to the cavity wall surface. i.e. the distance between the optical system and cavity wall surface. The distance information thus obtained is supplied to the section line forming circuit 21 to derive the imaged data representing the locus of the section line. The image data of the section line thus derived is supplied via the video processor unit 43 to the optical image display device 22, and the section image of the ultrasonic sectional image is displayed in the superimposed manner with the optical image of the cavity.

The present invention is not limited to the embodiments explained above, but many modifications and alternations may be conceived by those skilled in the art within the scope of the invention.

As explained above in detail, according to the invention, it is possible to display the image of the section line of the ultrasonic image in a superimposed manner with the optical image by providing means for measuring the distance between the distal end of the endoscope and the surface of the cavity wall and means for displaying the section line in accordance with the measured distance, so that the positional relationship between the ultrasonic image and the optical image can be confirmed easily and accurately and thus the diagnosis can be carried out precisely and promptly.

What is claimed is:
1. An ultrasonic endoscope apparatus comprising:
an endoscope having an insertion section which is insertable into a cavity of a body under inspection;
optical image observing means for forming an optical image of the cavity and having an objective lens arranged in a distal end of said insertion section of said endoscope;
ultrasonic image observing means for forming an ultrasonic sectional image of the cavity and having at least one ultrasonic vibrating element arranged in the distal end of said insertion section of said endoscope; and means for obtaining image data representing a section line of the ultrasonic sectional image;

display means, responsive to said optical image observing means and said means for obtaining said section line image data, for displaying an image of said section line of the ultrasonic sectional image and said optical image of the cavity in a superimposed manner.

2. An apparatus according to claim 1, wherein said means for obtaining said section line image data comprises distance measuring means for measuring a distance between the objective lens of the optical image observing means and a surface of the cavity under inspection, and means for providing to said display means information representing the image of the section line in accordance with the distance measured by said distance measuring means.

3. An apparatus according to claim 2, wherein said distance measuring means comprises means for measuring the distance by processing an echo signal which is obtained by receiving an ultrasonic wave emitted by said ultrasonic vibrating element and reflected from the cavity.

4. An apparatus according to claim 3, wherein said distance measuring means comprises a comparator for extracting the first echo from the echo signals supplied from said ultrasonic vibrating element to generate a stop signal and a counter for detecting a time interval between a start signal and the stop signal by counting clock pulses during said time interval, said start signal being generated in synchronism with the generation of the ultrasonic wave from said ultrasonic vibrating element, said means for obtaining said section line image data including a section line forming circuit for deriving said distance between the objective lens and the cavity as a distance between the ultrasonic vibrating element and the cavity in accordance with a count value of said counter and for deriving image data representing a locus of the section line on the optical image, and said display means including a section line display device for displaying the image of the section line in accordance with the image data.

5. An apparatus according to claim 4, wherein said optical image observing means comprises an image guide for transmitting an optical image of the cavity formed by said objective lens, and an eyepiece section for observing the optical image of the cavity transmitted through the image guide, and said section line display device is constructed each that the image of the section line is monitored by means of said eyepiece section.

6. An apparatus according to claim 5, wherein said section line display device is constructed as an adaptor which can be detachably secured to the eyepiece section.

7. An apparatus according to claim 5, wherein said section line display device is constructed as an adaptor which can be detachably inserted between an outlet of the image guide and the eyepiece section.

8. An apparatus according to claim 4, wherein said optical image observing means comprising an image sensing device arranged in the distal end of the endoscope and receiving the image of the cavity formed by the objective lens to produce an optical image signal and said display means is a single display device for displaying said optical image of the cavity in accordance with the optical image signal and said image of said section line.

9. An apparatus according to claim 2, wherein first and second ultrasonic vibrating elements are provided in the distal end of the endoscope, one of which is used to observe the ultrasonic sectional image and the other of which is used to measure the distance.

10. An ultrasonic endoscope apparatus comprising:

an endoscope having an insertion section which is insertable into a cavity of a body under inspection;

optical image observing means for forming an optical image of the cavity and having an objective lens arranged in a distal end of said insertion section of said endoscope;

ultrasonic image observing means for forming an ultrasonic image sectional image of the cavity and having at least one ultrasonic vibrating element arranged in the distal end of said insertion section of said endoscope; and section line display means for displaying an image of a section line of the ultrasonic sectional image in a superimposed manner with the optical image of the cavity, wherein said section line display means comprises distance measuring means for measuring a distance between the objective lens of the optical image observing means and a surface of the cavity under inspection, and means for displaying the image of the section line in accordance with the distance measured by said distance measuring means.

11. An apparatus according to claim 10, wherein said distance measuring means comprises means for measuring the distance by processing an echo signal which is obtained by receiving an ultrasonic wave emitted by said ultrasonic vibrating element and reflected from the cavity.

12. An apparatus according to claim 11, wherein said distance measuring means comprises a comparator for extracting the first echo from the echo signals supplied from said ultrasonic vibrating element to generate a stop signal, a counter for detecting a time interval between a start signal and the stop signal by counting clock pulses during said time interval, said start signal being generated in synchronism with the generation of the ultrasonic wave from said ultrasonic vibrating element, a section line forming circuit for deriving said distance between the objective lens and the cavity as a distance between the ultrasonic vibrating element and the cavity in accordance with a count value of said counter and deriving an image data representing a locus of the section line on the optical image, and a section line display device for displaying the image of the section line in accordance with the image data.

13. An apparatus according to claim 12, wherein said optical image observing means comprises an image guide for transmitting an optical image of the cavity formed by said objective lens, and an eyepiece section for observing the optical image of the cavity transmitted through the image guide, and said section line display device is constructed such that the image of the section line is monitored by means of said eyepiece section.

14. An apparatus according to claim 13, wherein said section line display device is constructed as an adaptor which can be detachably secured to the eyepiece section.

15. An apparatus according to claim 13, wherein said section line display device is constructed as an adaptor which can be detachably inserted between an outlet of the image guide and the eyepiece section.

16. An apparatus according to claim 12, wherein said optical image observing means comprises an image sensing device arranged in the distal end of the endoscope and receiving the image of the cavity formed by the objective lens to produce an optical image signal and an optical image display device for displaying the optical image of the cavity in accordance with the optical image signal, and said section line display device and said optical image display device are commonly formed as a single display device.

17. An apparatus according to claim 10, wherein first and second ultrasonic vibrating elements are provided in the distal end of the endoscope, one of which is used to observe the ultrasonic sectional image and the other of which is used to measure the distance.

* * * * *